(12) United States Patent
Beebe et al.

(10) Patent No.: US 9,486,287 B2
(45) Date of Patent: Nov. 8, 2016

(54) DISPOSABLE PROTECTIVE COVERS AND ASSOCIATED DISPENSING SYSTEM FOR USE ON STETHOSCOPES AND OTHER ITEMS

(71) Applicants: Matthew W. Beebe, Zionsville, IN (US); Neil S. Epstein, Wayne, PA (US); Stephen T. Epstein, Newtown, PA (US); Robert M. Sanfilippo, Glendale, CA (US)

(72) Inventors: Matthew W. Beebe, Zionsville, IN (US); Neil S. Epstein, Wayne, PA (US); Stephen T. Epstein, Newtown, PA (US); Robert M. Sanfilippo, Glendale, CA (US)

(73) Assignee: CoreShieldz, LLC, Huntingdon Valley, PA (US)

( * ) Notice: Subject to any disclaimer, the term of this patent is extended or adjusted under 35 U.S.C. 154(b) by 444 days.

(21) Appl. No.: 14/082,716

(22) Filed: Nov. 18, 2013

(65) Prior Publication Data

US 2015/0136896 A1    May 21, 2015

(51) Int. Cl.
*A61B 19/02* (2006.01)
*A61B 19/04* (2006.01)
*H05K 5/03* (2006.01)

(52) U.S. Cl.
CPC ............ *A61B 19/045* (2013.01); *A61B 46/10* (2016.02); *A61B 50/30* (2016.02); *H05K 5/03* (2013.01); *Y10T 428/15* (2015.01)

(58) Field of Classification Search
CPC ...... H05K 5/03; A61B 19/02; A61B 19/045; B65B 67/05; B65H 2402/41; B65H 35/002; B65H 37/005; B65H 49/205; B65H 45/406
See application file for complete search history.

(56) References Cited

U.S. PATENT DOCUMENTS

| | | | | |
|---|---|---|---|---|
| 5,202,169 | A * | 4/1993 | Spendlove | B42F 1/00 24/67 AR |
| 5,448,025 | A * | 9/1995 | Stark | A61B 7/02 181/131 |
| 5,511,689 | A | 4/1996 | Frank | |
| 5,534,346 | A | 7/1996 | Robinson | |
| 5,587,561 | A * | 12/1996 | Budayr | A61B 7/02 181/131 |
| 5,686,706 | A * | 11/1997 | Wurzburger | A61B 7/026 181/131 |
| 6,206,134 | B1 * | 3/2001 | Stark | A61B 7/02 181/131 |
| 7,117,971 | B1 * | 10/2006 | Cornacchia | A61B 7/02 181/131 |
| 7,424,929 | B1 * | 9/2008 | Martinez | A61B 7/02 181/131 |

(Continued)

*Primary Examiner* — Emmanuel M Marcelo
(74) *Attorney, Agent, or Firm* — LaMorte & Associates, P.C.

(57) ABSTRACT

A protective cover used to cover the head of a stethoscope and other items that contact the human body. The protective cover is made from a substrate film. The substrate film has opposing curved edges and opposing flat edges. Tab material is applied to the substrate film proximate the opposing curved edges. A coating of tacky adhesive is applied to the bottom surface of the substrate film between the tab material and between the opposing flat edges. The protective covers can be interconnected as a continuous chain, whereby separate protective covers are torn away along perforations. The chain can be wound onto a roll. The roll is held in a box for storage and dispensing. A slot is formed in the box through which individual protective covers can be removed from the roll.

18 Claims, 8 Drawing Sheets

(56) References Cited

U.S. PATENT DOCUMENTS

| | | | | |
|---|---|---|---|---|
| 7,757,807 B1* | 7/2010 | Martinez | ............... | A61B 7/02 181/131 |
| 7,823,690 B2* | 11/2010 | Hirsch | ............... | A61B 7/02 181/131 |
| 7,891,462 B2* | 2/2011 | Hmayakyan | ............... | A61B 7/02 181/131 |
| 8,042,646 B2* | 10/2011 | Gross | ............... | A61B 7/02 181/131 |
| 8,662,244 B2* | 3/2014 | Fishberger | ............... | A61B 19/026 181/131 |
| 2001/0045319 A1* | 11/2001 | Kemper | ............... | A61B 7/02 181/131 |
| 2002/0179094 A1* | 12/2002 | Perlow | ............... | A61B 19/54 128/897 |
| 2007/0272362 A1* | 11/2007 | Peterson | ............... | B65H 37/002 156/764 |
| 2009/0014232 A1 | 1/2009 | Hirsch et al. | | |
| 2009/0229732 A1* | 9/2009 | Determan | ............... | B32B 7/12 156/60 |
| 2012/0211171 A1* | 8/2012 | Patel | ............... | B29C 63/0004 156/538 |
| 2014/0319000 A1 | 10/2014 | Fishberger et al. | | |

\* cited by examiner

DISPOSABLE PROTECTIVE COVERS AND ASSOCIATED DISPENSING SYSTEM FOR USE ON STETHOSCOPES AND OTHER ITEMS

BACKGROUND OF THE INVENTION

1. Field of the Invention

In general, the present invention relates to stethoscope covers and similar sanitary covers. The present invention also relates to systems for dispensing disposable protective covers.

2. Prior Art Description

In any area of medicine, the use of uncontaminated equipment is imperative when treating patients. Otherwise, healthy patients can be cross-contaminated by the diseases of other patients simply by coming into contact with items in a physician's office.

One of the most common items that a patient contacts in a physician's office is a stethoscope. Stethoscopes are used by physicians to hear a patient's heartbeat, breathing, and other internal anatomic functions. However, although a stethoscope directly contacts the skin of patients, stethoscopes are rarely sterilized between patients. Consequently, as the stethoscope is moved from one patent to another, contamination can also be passed from one patient to another.

In an attempt to limit cross contamination created by the use of stethoscopes, protective covers have been developed for the stethoscope. The protective covers prevent the stethoscope from directly touching a patient. Furthermore, the protective covers are disposable so that a new clean cover can be used for each patient.

Protective covers attach to stethoscopes in one of two manners. In a first manner, protective covers attach adhesively to the head of the stethoscope. Such prior art covers are exemplified by U.S. Pat. No. 6,206,134 to Stark, entitled Cover For Stethoscope Head. In a second manner, protective covers attach mechanically to the head of a stethoscope, using an elastic band. Such prior art protective covers are exemplified by U.S. Pat. No. 7,891,462 to Hmayakyan, entitled Stethoscope Cover And Dispenser Therefore. However, in the prior art, both adhesively attached protective covers and mechanically attached protective covers have certain innate disadvantages.

Stethoscope heads come in a very large variety of shapes and sizes. It is therefore difficult to make any protective cover that fits all stethoscope heads well. Mechanical attachment systems simply do not work if the stethoscope head is either too large or too small, as compared to some predetermined optimal size. Adhesive attachment systems work on most sizes of stethoscopes. However, mismatches in size between the protective cover and the stethoscope head often leave exposed areas of adhesive on the protective cover. This adhesive grabs hair and clothing as the stethoscope is moved across the body. It also collects dirt and contaminants that can contact the stethoscope. Furthermore, after many adhesive-backed protective covers are attached to and removed from a stethoscope, the adhesive tends to build up on the stethoscope. The build up of adhesive makes the head of the stethoscope sticky. It, therefore, begins to easily harbor dirt and contaminants, therein negating the primary goal of keeping the stethoscope clean.

A need therefore exists for a stethoscope cover that can adhere to all sizes of stethoscope heads, yet does so without exposing adhesive and without having adhesive build up on the stethoscope. A need also exists for a system of dispensing protective covers for stethoscopes that keeps the covers clean and provides for easy attachment of the protective cover to the stethoscope. These needs are met by the present invention as described and claimed below.

SUMMARY OF THE INVENTION

The present invention is a protective cover that can be used to cover the head of a stethoscope and other items that contact the human body. The protective cover is made from a substrate film. The substrate film has a top surface and an opposite bottom surface. Both surfaces are confined within a periphery having two opposing flat edges and two opposing curved edges.

Tab material is applied to the substrate film proximate the opposing curved edges. A coating of tacky adhesive is applied to the bottom surface of the substrate film between the tab material and between the opposing flat edges. The coating of tacky adhesive does not cover the tab material.

The protective covers can be interconnected as a continuous chain, whereby separate protective covers are torn away along perforations. The chain can be wound onto a roll. The roll is held in a box for storage and dispensing. A slot is formed in the box through which individual protective covers can be removed from the roll.

BRIEF DESCRIPTION OF THE DRAWINGS

For a better understanding of the present invention, reference is made to the following description of exemplary embodiments thereof, considered in conjunction with the accompanying drawings, in which.

DETAILED DESCRIPTION OF THE DRAWINGS

Although the present invention stethoscope cover and dispensing system can be embodied in many ways, only one embodiment is illustrated. The exemplary embodiment is selected in order to set forth one of the best modes contemplated for the invention. The illustrated embodiment, however, is merely exemplary and should not be considered a limitation when interpreting the scope of the appended claims.

Figure 1:
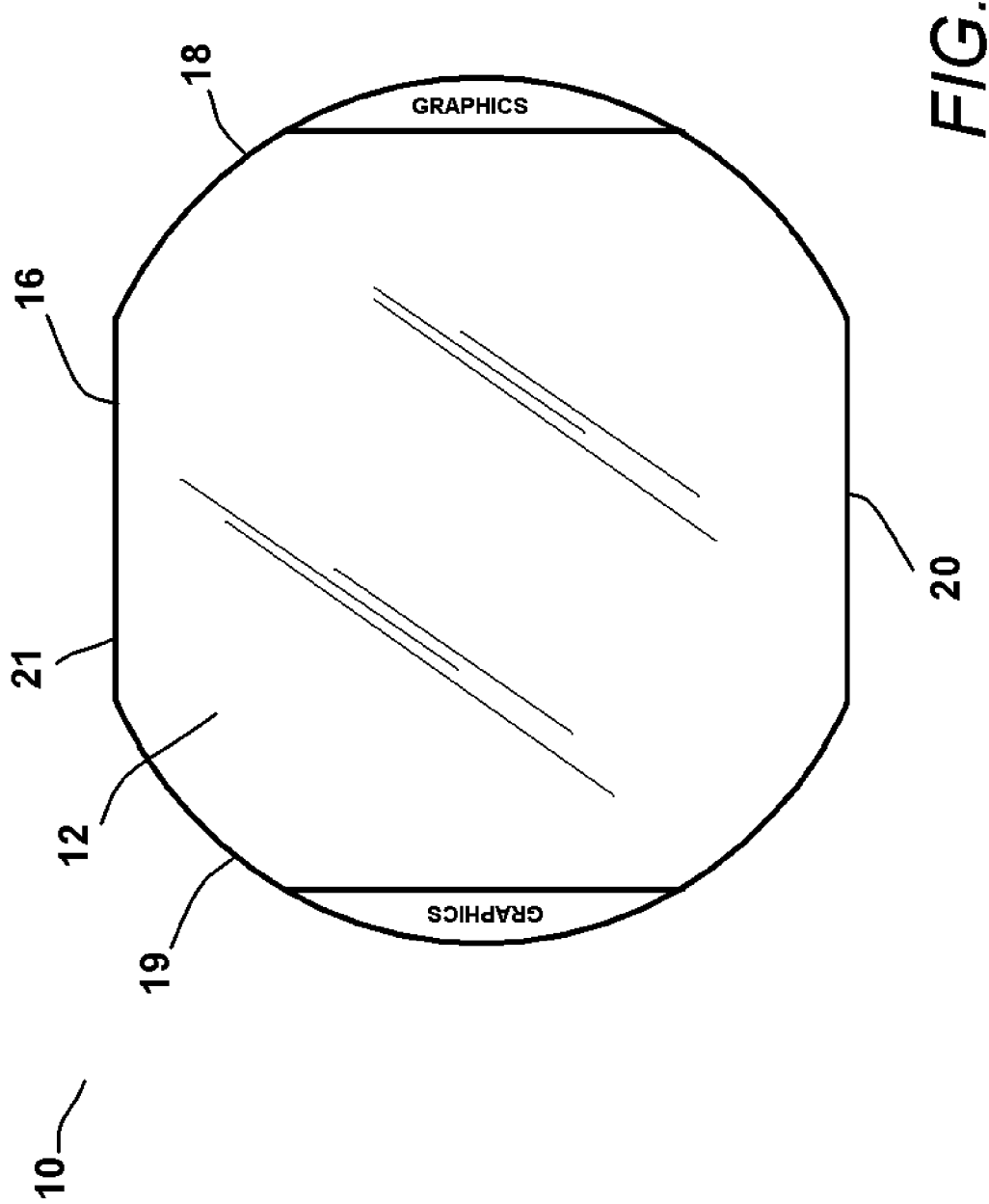
FIG. 1 is a top view of an exemplary embodiment of a protective cover.
Figure 2:
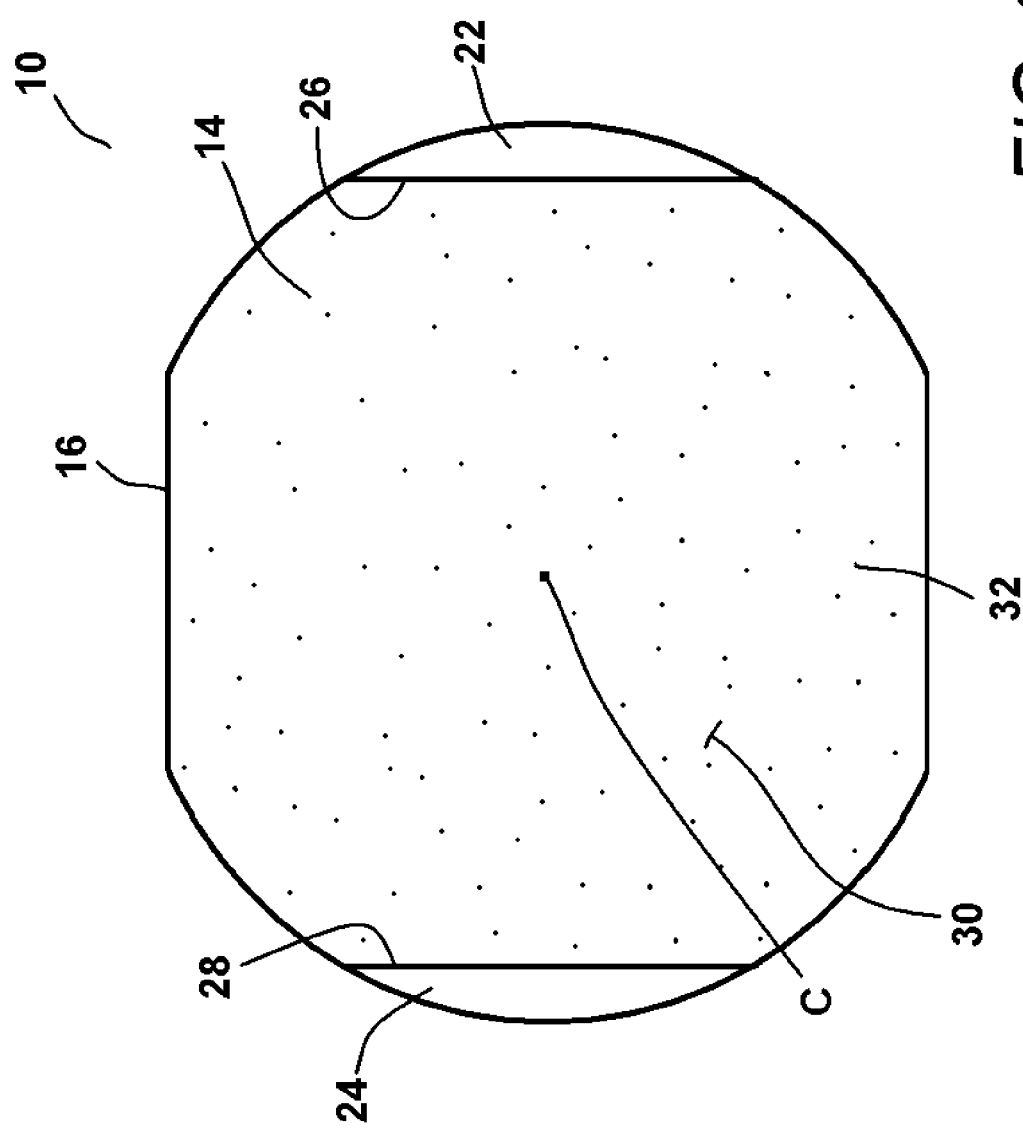
FIG. 2 is a bottom view of the exemplary embodiment of FIG. 1.

Referring to FIG. 1 and FIG. 2, the top surface 12 and bottom surface 14 of a protective cover 10 are shown. The protective cover 12 is made of a thin flexible substrate film 16. The substrate film 16 is preferably transparent and has a weight of less than one gram. The substrate film 16 is preferably a thin film of polyethylene. However, substrate films of cellophane and polypropylene can also be used.

The protective cover 10 has a top surface 12 (FIG. 1) and a bottom surface 14 (FIG. 2). The thickness of the substrate film 16 is preferably no greater than 0.2 millimeters. The protective cover 10 is symmetrically shaped around a center point C in the geometric center of both the top surface 12 and the bottom surface 14.

When viewed from either the top surface 12 or the bottom surface 14, it can be seen that the protective cover 10 has two opposing curved edges 18, 19 and two opposing straight edges 20, 21. The straight edges 20, 21 are parallel. The curved edges 18, 19 extend from one straight edge to the other. Each of the curved edges 18, 19 has a radius of curvature as measured from the center point C. The preferred radius of curvature is between 1 centimeter and 2 centimeters.

The top surface 12 of the protective cover 10 is an exposed area of the substrate film 16. However, on the bottom surface 14 of the protective cover 10, the substrate film 16 is covered by different materials. Two sections of the protective cover 10, adjacent the curved edges 18, 19, are covered with paper tabs 22, 24. The paper tabs 22, 24 are permanently adhered to the substrate film 16. The paper tabs 22, 24 are preferably paper, but can be Mylar or another readily printable substrate. The paper tabs 22, 24 contain graphics or indicia that identify the product and can be viewed through the substrate film 16 from the top surface 12 of the protective cover 10.

The paper tabs 22, 24 have straight sides 26, 28 that face each other. The preferred distance between the straight sides 26, 28 of the paper tabs 22, 24 is equal to the distance between the straight edges 20, 21 of the substrate film 16. The straight sides 26, 28 of the paper tabs 22, 24 and the straight edges 20, 21 of the substrate film 16 define a central region 30 on the bottom surface 14 of the substrate film 16.

The central region 30 of the bottom surface 14 is at least sporadically coated with an ultra thin coating of a tacky adhesive 32. The tacky adhesive 32 is acrylic based, being a mostly ester derivative of acrylic, methacrylic or cyanacylic acids. The adhesive is mixed with a softening agent, such as mineral oil, so that the adhesive becomes merely tacky when pressed against a surface. The tacky adhesive 32 is preferably less than 50 microns thick. At this level of thickness, the tacky adhesive 32 presents some unique characteristics. First, the tacky adhesive 32 does not adhere well to skin or hair because the natural oils on skin and hair counteract the tacky nature of the adhesive and make the tacky adhesive 32 ineffective. Second, the tacky adhesive 32, once cured onto the bottom surface 14 of the substrate film, is capable of temporarily adhering to the top surface 12 of the substrate film without losing any adhesive properties. In this manner, when the protective cover 10 rolls onto itself or onto another protective cover, it can be readily unrolled like a roll of tape. The tacky adhesive 32 is just adequate to retain the small weight of the protective cover 10 when pressed against the head of a stethoscope. The tacky adhesive 32 does not cover the paper tabs 22, 24 on either side of the central region 30. As such, the paper tabs 22, 24 are not tacky to the touch and do not adhere to contacted surfaces.

Figure 3:
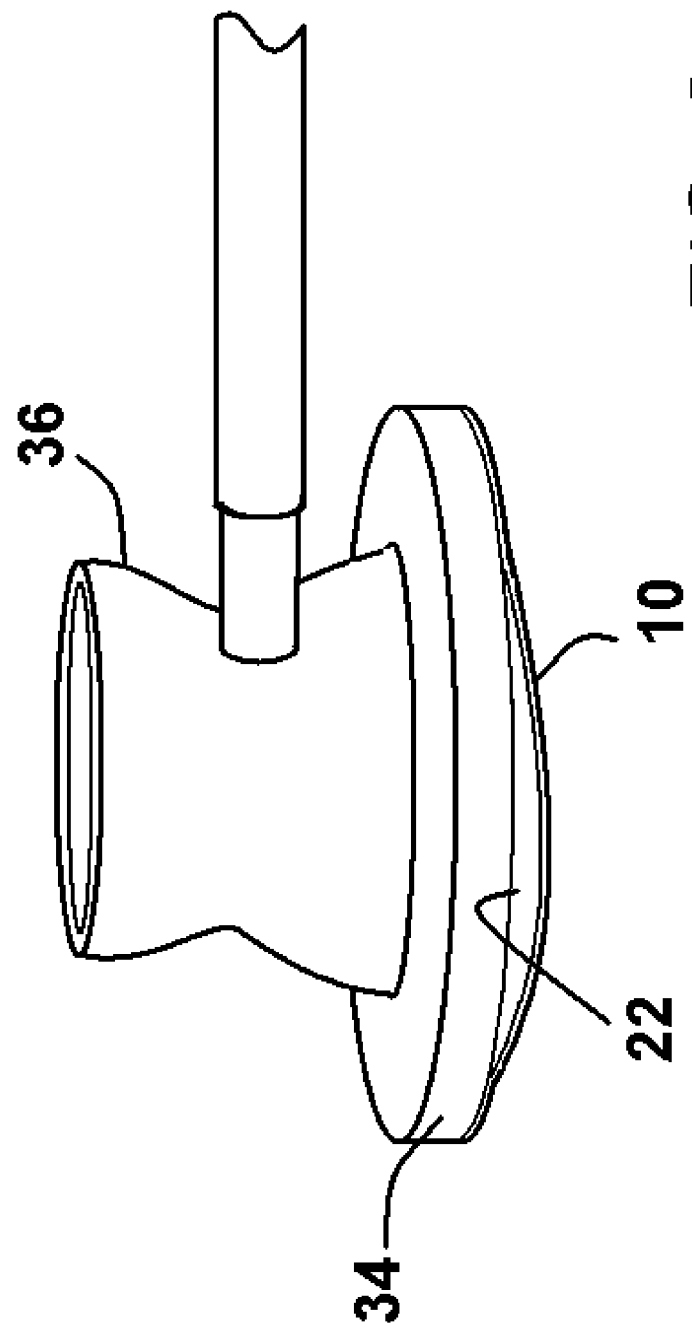
FIG. 3 is a perspective view of a protective cover being applied to an ideally sized head of a stethoscope.

The protective cover 10 can be used on stethoscopes having a wide range of shapes and sizes. Ideally, the head of the stethoscope has a diameter equal to the distance between the straight edges 20, 21 of the substrate film 16. This is shown in FIG. 3. Referring to FIG. 3 in conjunction with FIG. 1 and FIG. 2, it can be seen that the protective cover 10 completely covers the head 34 of the stethoscope 36. Furthermore, none of the tacky adhesive 32 on the bottom surface 14 of the substrate film 16 is exposed. However, the paper tabs 22, 24 extend beyond the periphery of the head 34 of the stethoscope 36. As a result, the paper tabs 22, 24 are very easy to grasp. This makes the protective cover 10 easy to apply to the head 34 of the stethoscope 36 and easy to remove.

Figure 4:
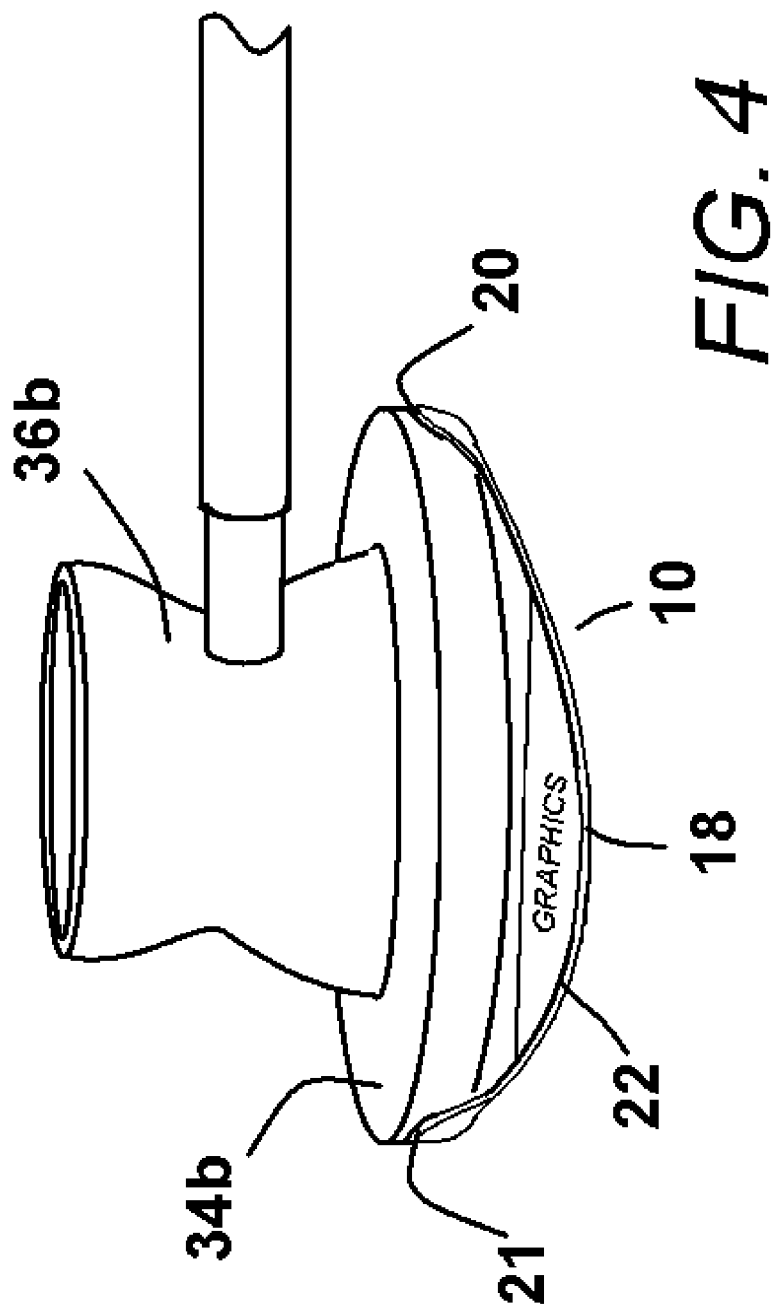
FIG. 4 is a perspective view of a protective cover being applied to an undersized head of a stethoscope.

Referring to FIG. 4 in conjunction with FIG. 1 and FIG. 2, it can be seen that the protective cover 10 can also be used on the head 34b of a stethoscope 36b that has a diameter that is smaller than the distance between the paper tabs 22, 24 on the substrate film 16. In this scenario, the head 34b of the stethoscope 36b is placed in the center of the protective cover 10. If the straight edges 20, 21 of the protective cover 10 extend beyond the head 34b of the stethoscope 36b, then those edges can be folded up against the sides of the head 34b. Since the straight edges 20, 21 are truncated, they tend not to protrude above the head 34b of the stethoscope 36b. This manipulation causes the curved edges 18, 19 of the protective cover 10 to extend beyond the head 34b of the stethoscope 36b. However, the paper tabs 22, 24 are attached to the substrate film 16 at the curved edges 18, 19. The paper tabs 22, 24, therefore, extend from the head 34b of the stethoscope 36b. The paper tabs 22, 24 contain no tacky adhesive. As a result, little or none of the tacky adhesive 32 is exposed even though the protective cover 10 is larger than the head 34b of the stethoscope 36b.

If the protective cover 10 is used to cover the head of a stethoscope that is much larger than the area of the protective cover 10, it will be understood that the protective cover 10 can be attached to the center of the head. The center of the head of the stethoscope will therefore be protected. The peripheral areas of the head of the stethoscope that are not covered remain unprotected. However, the stethoscope can be used in the normal manner and some protection is better than no protection at all.

Figure 5:
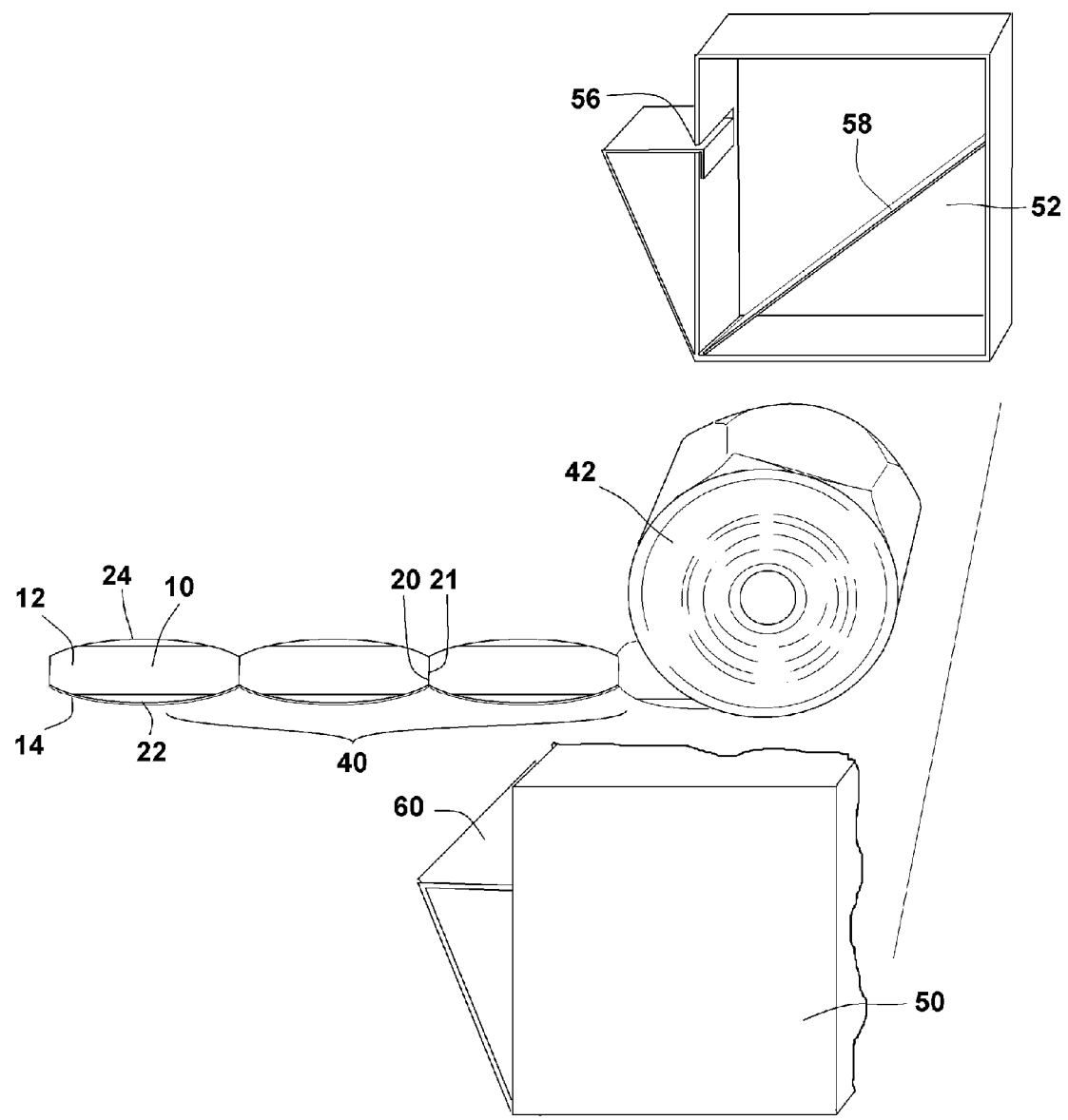
FIG. 5 is a perspective view of a rolled chain of protective covers in a dispensing box.

Referring to FIG. 5 in conjunction with FIG. 1 and FIG. 2, it can be seen that each protective cover 10 is manufactured as part of a continuous chain 40, where numerous protective covers 10 are interconnected end-to-end. The continuous chain 40 is wound into a roll 42 so that tacky adhesive 32 on the bottom surface 14 of each protective cover 10 rolls into contact with the top surface 12 of a different protective cover 10. No removable protective strip is used to cover the tacky adhesive 32. This reduces costs, simplifies manufacture, and enables more protective covers 10 to be wound on the roll 42.

When the protective cover 10 is wound into the roll 42, the paper tabs 22, 24 are positioned along the sides of the roll 42. As such, there is no adhesive exposed along the sides of the roll 42. This isolates the tacky adhesive 32 toward the center of the roll 42. In this manner, should the roll 42 rub against the inside of its dispenser box or should the roll 42 become exposed to dust or other contaminants, the tacky adhesive 32 does not become compromised by such contact and contaminants. The presence of the paper tabs 22, 24 along the sides of the roll 42 also ensures that the individual protective covers 10 easily peel away from the roll 42.

On the roll 42, the individual protective covers 10 are joined in a chain 40 by their straight edges 20, 21. The straight edges 20, 21 are perforated to enable individual protective covers 10 to be selectively removed from the roll 42. The roll 42 is packaged, sold, and distributed in a specialized box 50.

Figure 6:
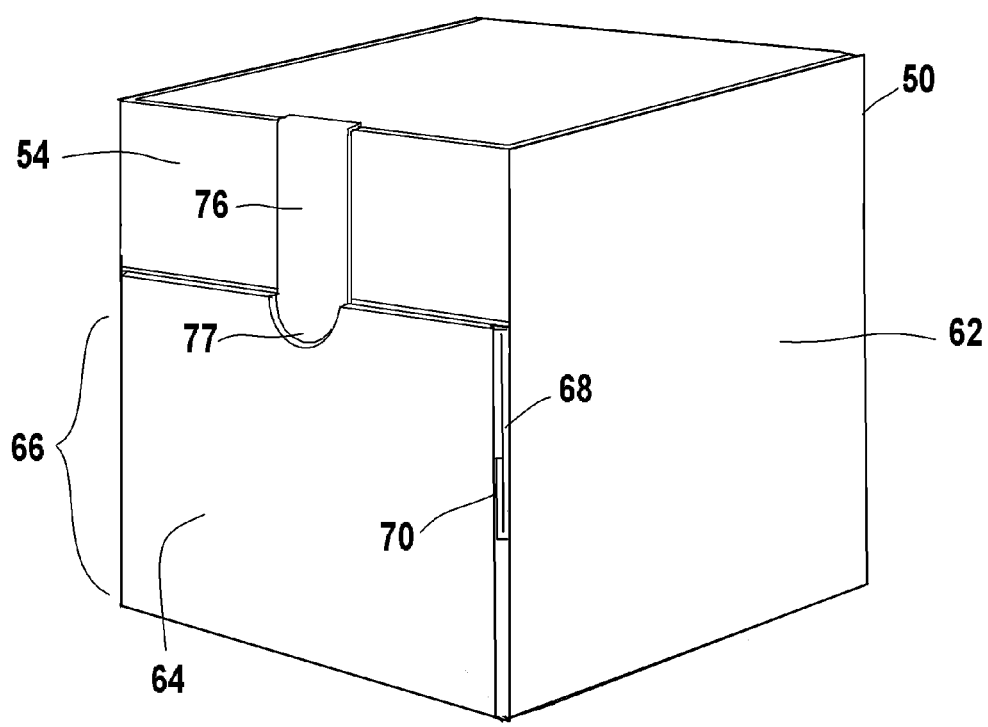
FIG. 6 shows the dispensing box configured for storage and shipping.
Figure 7:
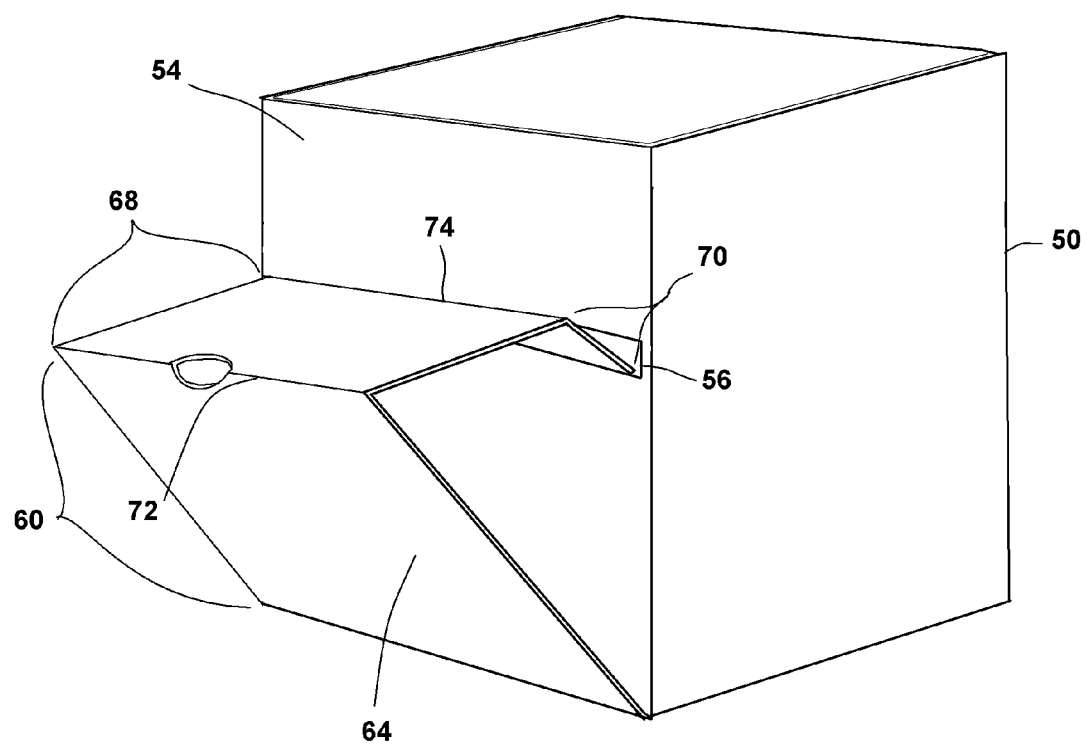
FIG. 7 shows the dispensing box being configured for dispensing.

Referring to FIGS. 6 and 7 in conjunction with FIG. 5, it can be seen that the box 50 defines an internal compartment 52 with a length, width, and height large enough to hold the roll 42.

The box 50 has a front surface 54. The front surface 54 contains a dispensing slot 56. The chain 40 of protective covers 10 extends through the dispensing slot 56 from the roll 42. Inside the box 50, an inclined internal ramp 58 is provided to guide the protective cover 10 and prevent the roll 42 from excessively recoiling inside the box 50.

A ledge 60 extends horizontally away from the front surface 54 of the box 50 directly under the dispensing slot 56. The ledge 60 has a width that is at least half as wide as a protective cover 10 is long. In this manner, at least half of the protective cover 10 is supported by the ledge 60 as a protective cover 10 extends from the box 50. The box 50 is made of a folded paperboard blank 62. The ledge 60 is made by a flap 64 in the paperboard blank 62. The flap 64 has a first section 66, a second section 68, and an end section 70. The first section 66 and the second section 68 are connected at a first fold line 72. The second section 68 and the end section 70 meet at a second fold line 74. As is indicated in FIG. 6, when the box 50 is shipped, the second section 68 and the end section 70 of the flap 64 are folded under the first section 66 of the flap 64. The first section 66 of the flap 64 is pressed against the front surface 54 of the box 50. A peel-away strip can be used to secure the flap 64. However, in the shown embodiment, a paperboard strip 76 is used to secure the flap 64 against the front surface 54 of the box 50. The paperboard strip engages the flap through a recess 77 and engages a fold at the top of the box 50.

Referring to FIG. 7 in conjunction with FIG. 6 and FIG. 5, it can be seen that to open the box 50, the paperboard strip 76 is removed. This frees the flap 64. The second section 68 of the flap 64 and the end section 70 of the flap 64 are unfolded. The end section 70 of the flap 64 is then inserted into the structure of the box 50 under the dispensing slot 56. This positions the second section 68 of the flap 64 into the form of the ledge 60 and the first section 66 as a support to the ledge 60.

Referring to FIGS. 5, 6 & 7, it will be understood that to dispense a protective cover 10 from the box 50, the paperboard strip 76 is removed and the flap 64 is configured into the ledge 60. The chain 40 of protective covers 10 is then advanced through the dispensing slot 56. This leaves one protective cover 10 exposed on the ledge 60 with its tacky adhesive 32 facing upwardly.

The protective cover 10 is grasped by the paper tabs 22, 24 and separated from the roll 42. The tacky adhesive 32 remains untouched. The protective cover 10 is then pressed against the head of a stethoscope. Due to the thinness of the protective cover 10, the presence of the protective cover 10 does not inhibit sound from transmitting into the stethoscope. After use, the protective cover 10 is removed from the stethoscope 10 and leaves no sticky residue in the head of the stethoscope.

Figure 8:
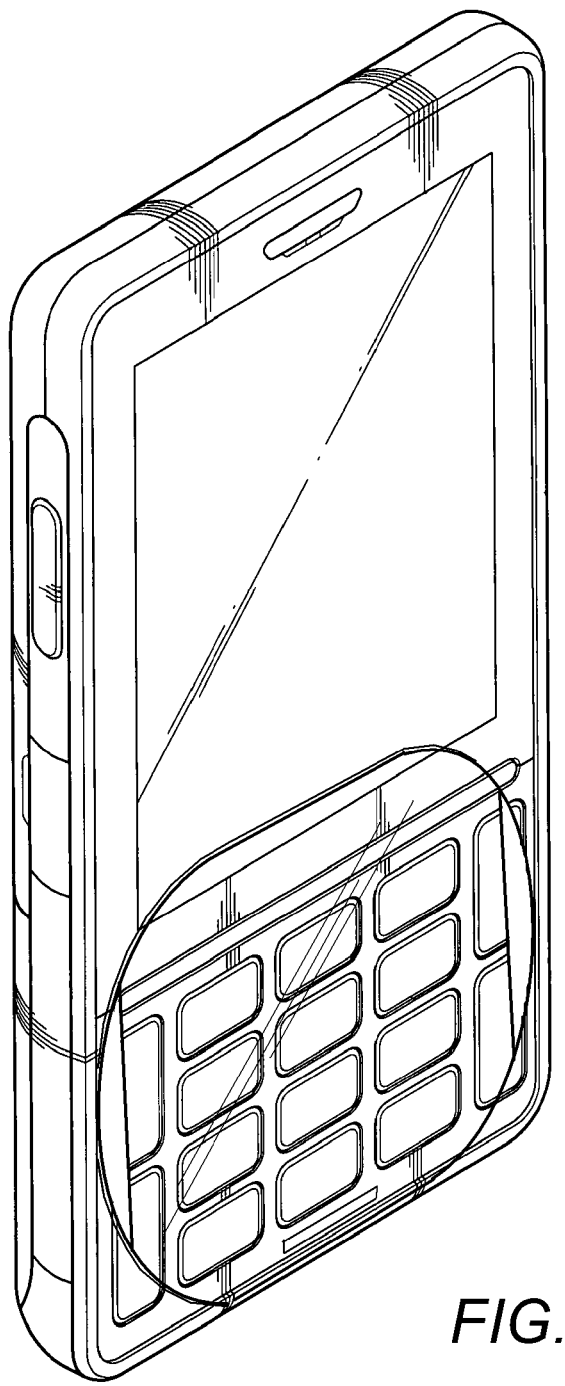
FIG. 8 shows the protective cover applied to a cell phone.

The protective cover 10 is an excellent barrier from bacterial contamination. The protective cover is also an excellent medium through which sound energy can pass. These features enable the protective cover to be used on other objects in addition to stethoscopes. Referring to FIG. 8, one such alternate embodiment is shown. In this embodiment, the protective cover 10 is placed over the microphone opening 82 of a telephone. Protective covers can also be placed on telephones, tablet computers, dictaphones, and any other such device that either records or transmits sound while coming into close contact with the user's body.

It will be understood that the embodiments of the present invention that are illustrated and described are merely exemplary and that a person skilled in the art can make many variations to those embodiments. For instance, the size and the shape of the protective cover can be customized for different applications. All such embodiments are intended to be included within the scope of the present invention as defined by the claims.

What is claimed is:

1. A protective cover, comprising:
    a substrate film having a top surface and a bottom surface, two opposing flat edges and two opposing curved edges, wherein said two opposing flat edges are a first distance apart;
    tab material applied to said substrate film proximate said opposing curved edges, wherein said opposing curved edges are spaced apart by a distance generally equal to said first distance;
    a coating of tacky adhesive applied to said bottom surface of said substrate film between said tab material and between said opposing flat edges, wherein said coating of tacky adhesive does not cover said tab material.

2. The protective cover according to claim 1, wherein said substrate film is transparent so that said tab material can be discerned through said substrate film from said top surface of said substrate film.

3. The protective cover according to claim 1, wherein said coating of tacky adhesive is less than 0.1 millimeters thick.

4. The protective cover according to claim 1, wherein said coating of tacky adhesive is an acrylic adhesive.

5. The protective cover according to claim 1, wherein graphics are printed on said tab material.

6. A protective cover assembly, comprising;
    a chain of interconnected protective covers, wherein each of said protective covers on said chain is defined between sets of perforations formed within said chain, wherein each of said sets of perforations is a first distance apart;
    wherein each of said protective covers has a substrate film having a top surface and a bottom surface that extend between said sets of perforations and two opposing curved edges;
    wherein tab material is applied to said substrate film proximate said opposing curved edges and are spaced apart by a distance generally equal to said first distance;
    and wherein a coating of tacky adhesive is applied to said bottom surface of said substrate film between said tab material without coating said tab material.

7. The assembly according to claim 6, wherein said substrate film is transparent so that said tab material can be discerned through said substrate film from said top surface of said substrate film.

8. The assembly according to claim 6, wherein said coating of tacky adhesive is less than 0.1 millimeters thick.

9. The assembly according to claim 6, wherein said coating of tacky adhesive is an acrylic adhesive.

10. The protective cover according to claim 6, wherein graphics are printed on said tab material.

11. The assembly according to claim 6, wherein said chain of interconnected protective covers is wound into a roll and said assembly further includes a box that retains said roll, wherein said box has a dispensing slot through which said chain extends.

12. The assembly according to claim 11, wherein said box includes a ledge that extends in front of said dispensing slot for supporting a section of said chain as it extends out of said dispensing slot.

13. The assembly according to claim 11, further including a ramp within said box that orients said roll within said box.

14. A protective cover assembly, comprising;
    a chain of interconnected protective covers, wherein each of said protective covers on said chain is defined between sets of perforations formed within said chain that enable individual protective covers to be separated from said chain, wherein each of said sets of perforations is a first distance apart;

wherein each of said protective covers has a substrate film having a top surface and a bottom surface that extend between said sets of perforations;

wherein tab material is applied to said substrate film at opposite sides of each of said protective covers and is spaced apart by a distance generally equal to said first distance;

and wherein a coating of tacky adhesive is applied to said bottom surface of said substrate film of each of said protective covers only between said tab material.

15. The assembly according to claim 14, wherein said substrate film is transparent so that said tab material can be discerned through said substrate film from said top surface of said substrate film.

16. The assembly according to claim 15, wherein graphics are printed on said tab material.

17. The assembly according to claim 14, wherein said chain of interconnected protective covers is wound into a roll and said assembly further includes a box that retains said roll, wherein said box has a dispensing slot through which said chain extends.

18. The assembly according to claim 17, wherein said box includes a ledge that extends in front of said dispensing slot for supporting a section of said chain as it extends out of said dispensing slot.

* * * * *